US00PP34086P2

(12) United States Plant Patent
Smulders

(10) Patent No.: US PP34,086 P2
(45) Date of Patent: Apr. 5, 2022

(54) APPLE TREE NAMED 'WURTWINNING'

(50) Latin Name: ***Malus domestica* Borkh.**
Varietal Denomination: Wurtwinning

(71) Applicant: FRESH FORWARD HOLDING B.V., ECK en Wiel (NL)

(72) Inventor: Marinus Johannes Maria Smulders, Wageningen (NL)

(73) Assignee: FRESH FORWARD HOLDING B.V., Eck en Wiel (NL)

( * ) Notice: Subject to any disclaimer, the term of this patent is extended or adjusted under 35 U.S.C. 154(b) by 0 days.

(21) Appl. No.: 17/175,523

(22) Filed: Feb. 12, 2021

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./156, 161
See application file for complete search history.

(56) References Cited

PUBLICATIONS

RheinlandPfalz website. 2018. https://www.obstbau.rlp.de/Internet/global/Themen.nsf/0/c125e7da51585146c12585050035c1c7/$FILE/Baab_Fischer_zukunftsf%C3%A4hige%20Apfelsorten.pdf. 3 pages. (Year: 2018).*

* cited by examiner

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of Apple tree named 'Wurtwinning', characterized by its upright to outwardly spreading plant habit; moderately vigorous growth habit; numerous fruit produced per plant; high quality fruits with bright red-colored skin; and resistance to Apple Scab and Powdery Mildew.

3 Drawing Sheets

Figure 1:
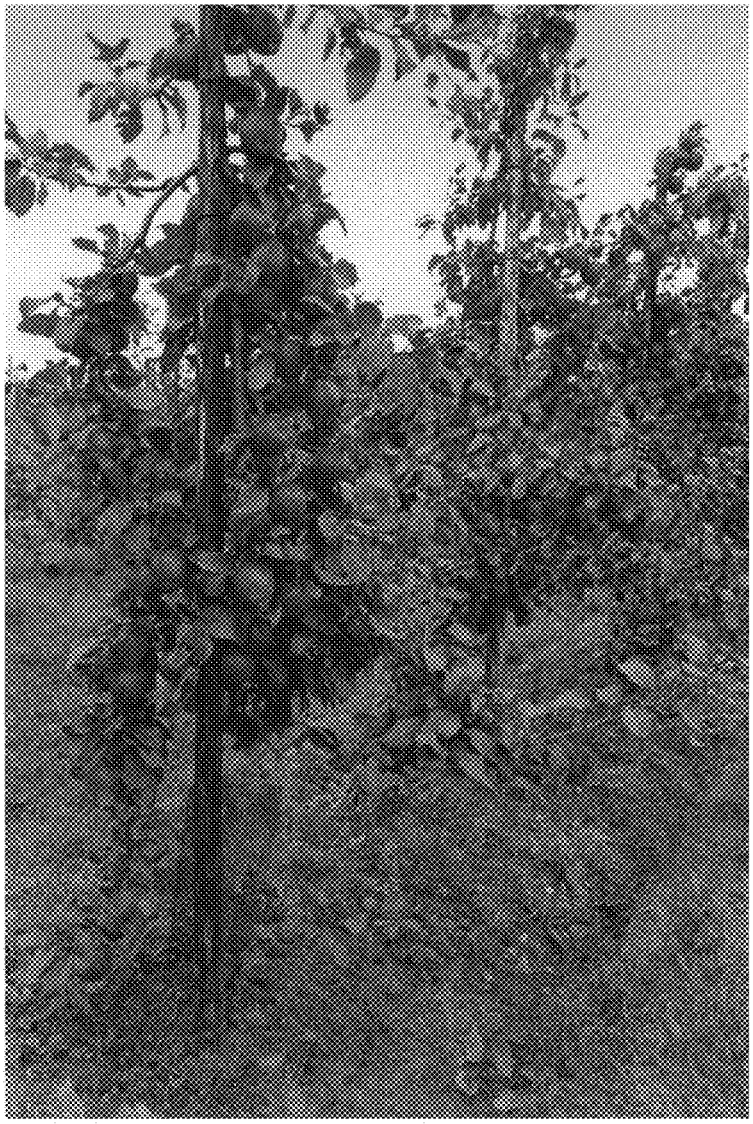

Botanical designation: *Malus domestica* Borkh.
Cultivar denomination: 'WURTWINNING'.

STATEMENT REGARDING PRIOR DISCLOSURES BY THE INVENTOR/APPLICANT & ASSIGNEE:

An European Community Plant Breeder's Rights application for the instant plant was filed by the Applicant/Assignee, Fresh Forward Holding B.V. of Eck en Wiel, The Netherlands on Sep. 14, 2018, application number 2018/2360. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of Apple tree, botanically known as *Malus domestica* Borkh. and hereinafter referred to by the name 'Wurtwinning'.

The new Apple tree is a product of a planned breeding program conducted by the Inventor in Elst, The Netherlands. The objective of the breeding program was to create new Apple trees that produce high quality fruits and that are resistant to Apple Scab (*Venturia inaequalis*) which causes severe surface blemishing of the fruit.

The new Apple tree originated from a cross-pollination conducted by the Inventor in Elst, The Netherlands in 2004 of *Malus domestica* Borkh. 'Honeycrisp', disclosed in U.S. Plant Pat. No. 7,197, as the female, or seed, parent with a proprietary selection of *Malus domestica* Borkh. identified as code number SQ 159, not patented, as the male, or pollen, parent. The new Apple tree was discovered and selected by the Inventor as a single plant within the progeny of the stated cross-pollination grown in a controlled environment in Elst, The Netherlands in 2010.

Asexual reproduction of the new Apple tree by grafting in a controlled environment in Randwijk, The Netherlands since 2012 has shown that the unique features of this new Apple tree are stable and reproduced true to type in successive generations.

SUMMARY OF THE INVENTION

The new Apple tree has not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Wurtwinning'. These characteristics in combination distinguish 'Wurtwinning' as a new and distinct Apple tree:

1. Upright to outwardly spreading plant habit.
2. Moderately vigorous growth habit.

3. Numerous fruit produced per plant.
4. High quality fruits with bright red-colored skin.
5. Resistant to Apple Scab and Powdery Mildew.

Trees of the new Apple differ primarily from trees of the female parent, 'Honeycrisp', in the following characteristics:

1. Leaves of trees of the new Apple are ovate to elliptic in shape whereas leaves of trees of 'Honeycrisp' are more ovate in shape.
2. Fruits of trees of the new Apple are more red in color than fruits of trees of 'Honeycrisp'.
3. Fruits of trees of the new Apple do not have stripes whereas fruits of trees of 'Honeycrisp' have stripes.

Trees of the new Apple differ primarily from trees of the male parent selection in the following characteristics:

1. Trees of the new Apple are more open in plant habit than trees of the male parent selection.
2. Leaves of trees of the new Apple are lighter green in color than leaves of trees of the male parent selection.
3. Fruits of trees of the new Apple are brighter red in color than fruits of trees of the male parent selection.

Trees of the new Apple can be compared to trees of *Malus domestica* 'Elstar', disclosed in U.S. Plant Pat. No. 6,450. In side-by-side comparisons, trees of the new Apple differ primarily from trees of 'Elstar' in the following characteristics:

1. Trees of the new Apple are more open in plant habit than trees of 'Elstar'.
2. Trees of the new Apple are less flexible than trees of 'Elstar'.
3. Trees of the new Apple have shorter lateral branches than trees of 'Elstar'.

Trees of the new Apple can be compared to trees of *Malus domestica* 'WUR37', disclosed in U.S. Plant Pat. No. 28,397. In side-by-side comparisons, trees of the new Apple differ primarily from trees of 'WUR37' in the following characteristics:

1. Trees of the new Apple have longer internodes than trees of 'WUR37'.
2. Leaves of trees of the new Apple are ovate to elliptic in shape whereas leaves of trees of 'WUR37' are more elliptic in shape.
3. Fruits of trees of the new Apple are more vivid red in color than fruits of trees of 'WUR37'.
4. Fruits of trees of the new Apple are ovoid in shape whereas fruits of trees of 'WUR37' are more obloid in shape.
5. Fruits of trees of the new Apple have much longer postproduction longevity than fruits of trees of 'WUR37'.
6. Trees of the new Apple are more resistant to Apple Scab and Powdery Mildew than trees of 'WUR37'.

BRIEF DESCRIPTION OF THE PHOTOGRAPHS

The accompanying photographs illustrate the overall appearance of the new Apple tree showing the colors as true as it is reasonably possible to obtain in colored reproductions of this type. Colors in the photographs may differ slightly from the color values cited in the detailed botanical description which accurately describe the colors of the new Apple tree.

The photograph on the first sheet (FIG. 1) comprises a side perspective view of typical trees of 'Wurtwinning' grown in an outdoor orchard.

Figure 2:
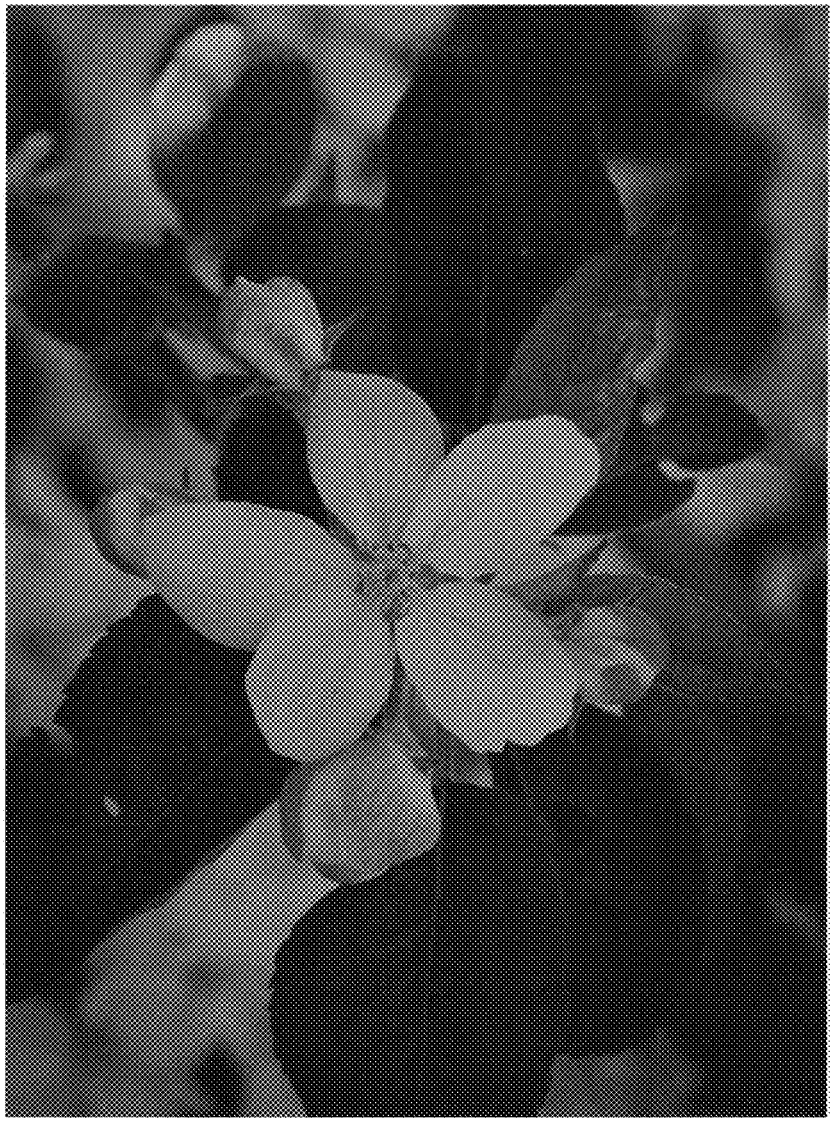

The photograph on the second sheet (FIG. 2) is a close-up view of a typical flowering branch of 'Wurtwinning'.

Figure 3:
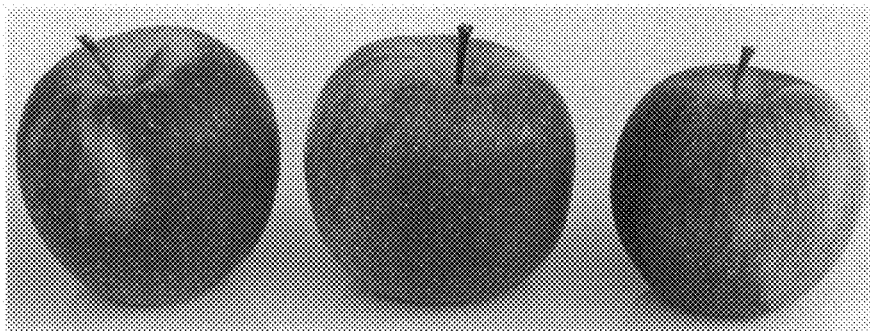

The photograph on the third sheet (FIG. 3) is a close-up view of typical fruits of 'Wurtwinning'.

DETAILED BOTANICAL DESCRIPTION

The aforementioned photographs, following observations and measurements describe trees grown during the summer in Randwijk, The Netherlands in an outdoor orchard and under cultural practices typical of commercial Apple tree production. Trees were four years old when the photographs and description were taken. During the production of the trees, day temperatures ranged from 10° C. to 24° C. and night temperatures ranged from 8° C. to 12° C. Measurements and numerical values represent averages for typical trees and tree parts. The actual measurements of any individual tree or tree parts, or any group of trees or tree parts, of the new Apple tree may vary from the stated average. In the following description, color references are made to The Royal Horticultural Society Colour Chart, 2001 Edition, except where general terms of ordinary dictionary significance are used.

Botanical classification: *Malus domestica* Borkh. 'Wurtwinning'.

Parentage:

*Female, or seed, parent.*—*Malus domestica* Borkh. 'Honeycrisp', disclosed in U.S. Plant Pat. No. 7,197.

*Male, or pollen, parent.*—Proprietary selection of *Malus domestica* Borkh. identified as code number SQ 159, not patented.

Propagation:

*Type.*—Typically by grafting onto a rootstock.

Plant description:

*Plant and growth habit.*—Upright to outwardly spreading plant habit; moderately vigorous growth habit and moderate growth rate.

*Tree height.*—About three meters.

*Tree diameter.*—About 1 meter to 1.5 meter.

*Trunk diameter.*—About 5 cm to 7 cm.

*Growth rate.*—About 20 cm to 30 cm per year.

*Lateral branch description.*—Length: About 40 cm to 70 cm. Diameter: About 3 cm to 5 cm. Internode length: About 5 cm to 12 cm. Strength: Strong, firm. Angle of attachment: About 80° from main trunk axis. Texture: Slightly to very slightly pubescent, woody and slightly rough. Color: Close to N200A.

*Leaf description.*—Arrangement: Alternate; simple. Length: About 7 cm to 10 cm. Width: About 3 cm to 5 cm. Shape: Ovate to elliptic. Apex: Acute. Base: Blunt, cordate. Margin: Serrate. Texture, upper surface: Smooth, glabrous. Texture, lower surface: Rough, pubescent. Venation pattern: Pinnate. Color: Developing and fully developed leaves, upper surface: Close to 137A; venation, close to 146D. Developing and fully developed leaves, lower surface: Close to 146A; venation, close to 146D. Petioles: Length: About 4 cm to 6 cm. Diameter: About 5 mm. Texture, upper and lower surfaces: Smooth, glabrous. Color, upper and lower surfaces: Close to 146D.

Flower description:

*Flower type and flowering habit*.—Single rotate flowers arranged on panicles; freely flowering habit with about six to ten flowers per inflorescence; flowers face mostly outwardly.

*Fragrance*.—Faintly fragrant, pleasant.

*Natural flowering season*.—Continuously flowering in April and May in The Netherlands.

*Flower longevity*.—Flowers last about two weeks on the plant; flowers not persistent.

*Inflorescence height*.—About 3 cm to 5 cm.

*Inflorescence diameter*.—About 3 cm to 5 cm.

*Flower diameter*.—About 2 cm to 3 cm.

*Flower depth* (*height*).—About 0.5 cm to 1 cm.

*Flower buds*.—Length: About 1 cm to 2 cm. Diameter: About 1 cm to 1.5 cm. Shape: Oval to rounded. Texture: Smooth, glabrous. Color: Close to 63A.

*Petals*.—Quantity and arrangement: Typically five in a single whorl; not imbricate. Length: About 1 cm to 1.5 cm. Width: About 0.5 cm to 1 cm. Shape: Obovate to elliptic. Apex: Obtuse. Base: Cordate. Margin: Entire. Texture, upper and lower surfaces: Smooth, glabrous; satiny. Color: When opening and fully opened, upper surface: Close to 155C slightly tinged with close to 63D. When opening and fully opened, lower surface: Close to 155C flushed with close to 63A.

*Sepals*.—Quantity and arrangement: Typically five in a single whorl. Length: About 5 mm to 7 mm. Width: About 3 mm to 5 mm. Shape: Ovate to somewhat deltoid. Apex: Acute to obtuse. Base: Cordate. Margin: Entire. Texture, upper and lower surfaces: Smooth, glabrous. Color, upper and lower surfaces: Close to 148B to 148C; at the base and the apex, close to 187A.

*Pedicels*.—Length: About 3 cm to 5 cm. Diameter: About 2 mm to 4 mm. Strength: Moderately strong. Aspect: About 60° to 90° from stem. Texture: Smooth, glabrous. Color: Close to 147C with spots, close to 187A.

*Reproductive organs*.—Stamens: Quantity: About 20 per flower. Filament length: About 2 cm. Filament color: Close to 155C. Anther length: About 3 mm to 5 mm. Anther shape: Bi-lobed. Anther color: Close to 17A. Pollen amount: Scarce. Pollen color: Close to 158A. Pistils: Quantity: About five per flower. Pistil length: About 1.5 cm. Stigma shape: Trumpet-shaped. Stigma color: Close to 154A. Style length: Less than 1 cm. Style color: Close to 150A. Ovary color: Close to 144A.

Fruit description:

*Ripening time*.—About 160 to 170 days.

*Postproduction longevity*.—About 270 days in cold storage.

*Yield*.—Higher than average; about 20 kg to 25 kg per container.

*Use*.—Fresh market.

*Length*.—About 7 cm to 8 cm.

*Diameter*.—About 7 cm to 8 cm.

*Fruit weight*.—Typically individual fruits will weigh between 200 to 300 gr depending on environmental conditions.

*General shape in profile*.—Ovoid.

*Depth of cavity*.—Medium, about 1.2 cm.

*Width of cavity*.—About 3 cm.

*Fruit stalk length*.—Medium to long; about 2.8 cm to 3.2 cm.

*Fruit stalk diameter*.—About 2 mm.

*Fruit stalk color*.—Close to 176A.

*Fruit skin color*.—Ground color, more green than 8A, overlain with close to 46B to 46C.

*Lenticels*.—Quantity: Dense; about 200 per fruit. Length: About 2 mm to 3 mm.

*Flesh texture*.—Firm, compact.

*Flesh color*.—Close to 10D.

*Flavor*.—Rich, aromatic.

*Locules*.—Quantity per fruit: Five. Length: About 1 cm. Width: About 1 cm. Shape: Ovate.

*Seeds*.—Quantity per locule: None to about three depending on environmental conditions. Length: About 5 mm to 7 mm. Diameter: About 3 mm to 5 mm. Shape: Obovate to elliptic. Color: Close to 200A.

Temperature tolerance: The new Apple tree has been observed to tolerate temperatures ranging from about −20° C. to about 35° C.

Pathogen & pest resistance: Trees of the new Apple have been observed to be resistant to Apple Scab (*Venturia inaequalis*) and Powdery Mildew (*Podosphaera leucotricha*). Trees of the new Apple have not been observed to be resistant to pests and other pathogens common to Apple trees.

It is claimed:

1. A new and distinct Apple tree named 'Wurtwinning' as illustrated and described.

* * * * *